US008758232B2

(12) United States Patent
Graham et al.

(10) Patent No.: US 8,758,232 B2
(45) Date of Patent: Jun. 24, 2014

(54) ROBOTIC ARM

(75) Inventors: Andrew Crispin Graham, Bristol (GB); Robert Oliver Buckingham, Abingdon (GB)

(73) Assignee: Oliver Crispin Robotics Limited (GB)

( * ) Notice: Subject to any disclaimer, the term of this patent is extended or adjusted under 35 U.S.C. 154(b) by 260 days.

(21) Appl. No.: 12/978,979

(22) Filed: Dec. 27, 2010

(65) Prior Publication Data

US 2011/0174108 A1 Jul. 21, 2011

Related U.S. Application Data

(63) Continuation of application No. PCT/GB2009/001643, filed on Jun. 30, 2009.

(30) Foreign Application Priority Data

Jun. 30, 2008 (GB) .................................. 0811971.1

(51) Int. Cl.
*A61B 1/008* (2006.01)

(52) U.S. Cl.
USPC .......................................... 600/142; 600/145

(58) Field of Classification Search
USPC ................................ 74/490.05; 600/142, 145
See application file for complete search history.

(56) References Cited

U.S. PATENT DOCUMENTS

| | | | |
|---|---|---|---|
| 4,494,417 A | 1/1985 | Larson et al. | |
| 4,551,061 A | 11/1985 | Olenick | |
| 4,790,294 A * | 12/1988 | Allred et al. | 600/141 |
| 5,916,146 A * | 6/1999 | Allotta et al. | 600/141 |
| 6,941,974 B2 * | 9/2005 | Utaki | 138/120 |
| 2001/0021843 A1 | 9/2001 | Bosselmann et al. | |
| 2004/0165810 A1 | 8/2004 | Fujita | |
| 2007/0225563 A1 * | 9/2007 | Ogino | 600/130 |
| 2009/0123111 A1 | 5/2009 | Udd | |

FOREIGN PATENT DOCUMENTS

| | | |
|---|---|---|
| DE | 3704815 A1 | 8/1987 |
| DE | 4240435 A1 | 5/1994 |
| JP | 59115187 A | 7/1984 |
| JP | 9254078 A | 9/1997 |
| JP | 2000300511 A | 10/2000 |
| JP | 2001046320 A | 2/2001 |
| WO | 9933392 A1 | 7/1999 |
| WO | 0133165 A1 | 5/2001 |
| WO | 0216995 A2 | 2/2002 |
| WO | 2006013682 A1 | 2/2006 |
| WO | 2007023631 A1 | 1/2007 |
| WO | 2007077458 A1 | 7/2007 |
| WO | 2007109778 A1 | 9/2007 |
| WO | 2008097540 A2 | 8/2008 |

OTHER PUBLICATIONS

Great Britain Search Report; Application No. GB 0811971.1; May 19, 2009; 1 page.
International Preliminary Report on Patentability and Written Opinion of the International Searching Authority; PCT/GB2009/001643; Jan. 5, 2011; 8 pages.
International Search Report; PCT/GB2009/001643; Dec. 14, 2009; 2 pages.

\* cited by examiner

*Primary Examiner* — David M Fenstermacher
*Assistant Examiner* — Terence Boes
(74) *Attorney, Agent, or Firm* — St. Onge Steward Johnston & Reens LLC

(57) ABSTRACT

An elongate robotic arm comprising articulated segments and a channel that extends along the longitudinal axis of the arm and contains a stiffening member which includes a sensor for measuring the shape of the arm. Using the central channel for this purpose improves the ease and accuracy of shape measurement.

8 Claims, 4 Drawing Sheets

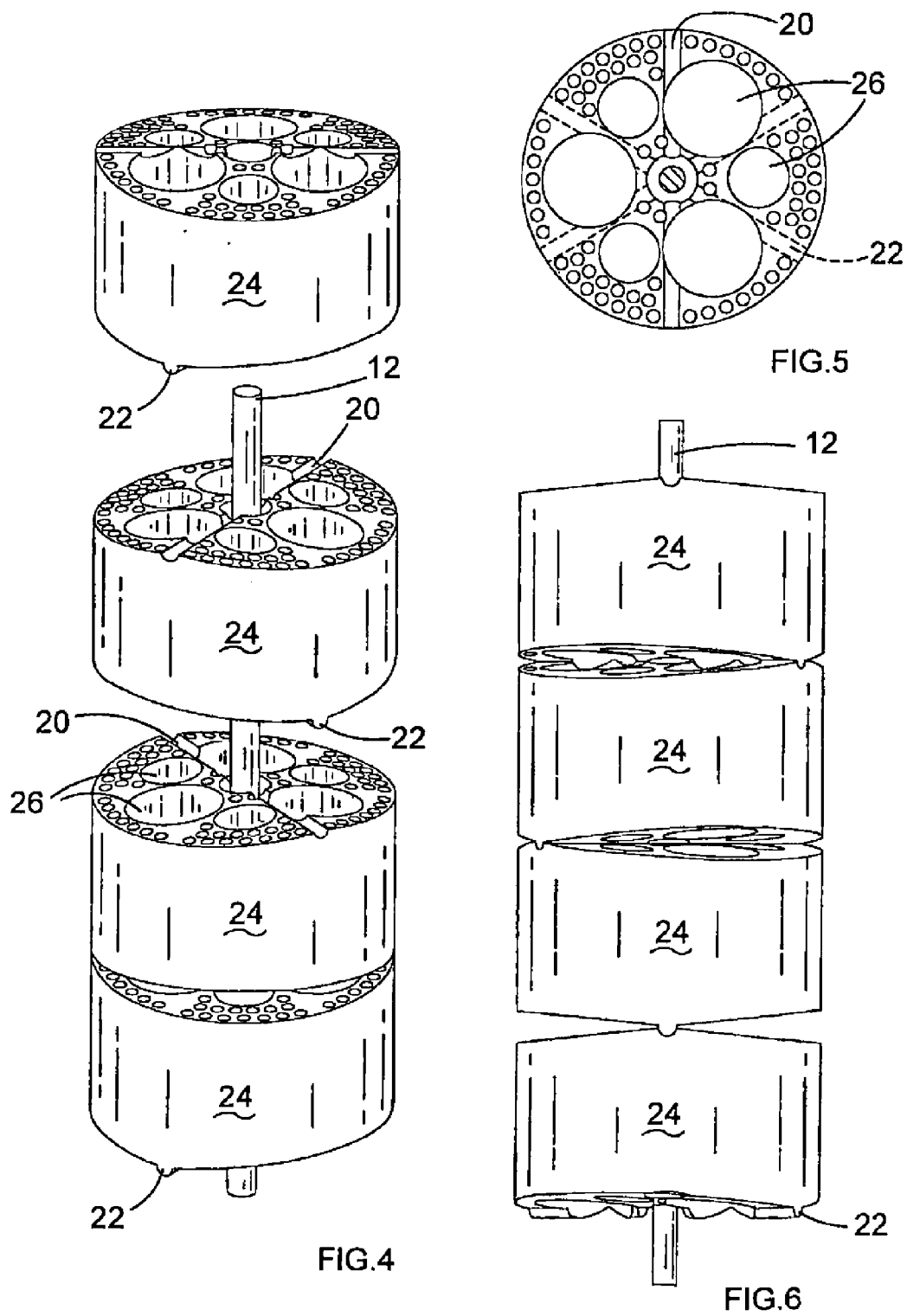

ROBOTIC ARM

CROSS-REFERENCE TO RELATED APPLICATIONS

The present application is a continuation of pending International patent application PCT/GB2009/001643 filed on Jun. 30, 2009 which designates the United States and claims priority from United Kingdom patent application 0811971.1 filed on Jun. 30, 2008, the content of which is incorporated herein by reference.

FIELD OF THE INVENTION

This invention relates to robotic arms and in particular to elongate arms comprising a plurality of sequentially arranged articulated links.

BACKGROUND OF THE INVENTION

Such articulated robotic arms are used particularly in situations wherein the arm is required to follow a path to a worksite with the body of the arm remaining on the path. This is known as "tip following", with the arm advancing along the path taken by the tip, in a snake-like manner. The tip may for example carry a work tool for carrying out a task.

A known type of device is described in our co-pending application WO 0216995. In such an arm, the links are grouped into segments each comprising a plurality of links, and the shape of the arm is controlled by control cables passing through the peripheries of the links. A set of cables evenly spaced around the links, for example 3, terminates at the most distal link of each segment, such that each set of cables may be used to control the orientation of that link, and thus the shape of the segment. The links each have a central aperture, which apertures together form a channel or lumen for carrying services usually associated with the work tool, for example cables controlling the tool or for communicating with the tool.

As the cables are located at the periphery of each link, the central channel or lumen may be relatively large. Since it is coaxial with the arm, the service cables will have a minimum effect on the bending and torsional stiffness of the arm.

In some types of arm, such as that described in our co-pending application WO 070774, a helical spring is provided around the central lumen, which provides stiffness to the arm so that it tends towards a straight configuration. The arm may be constructed by engaging the links one-by-one with the helical spring and screwing them down onto the adjacent link. The control and service cables may then be threaded through the apertures in the links.

With such arms, the shape of the arm can be detected or measured in various ways, as described in our copending application no WO 0613682. This usually involves mounting measuring devices around the periphery of the links to measure the space between adjacent links.

SUMMARY OF THE INVENTION

According to the present invention, there is provided an elongate robotic arm comprising a plurality of sequentially arranged articulated segments, a channel extending along the longitudinal axis of the arm, and an elongate stiffening member carried by the channel, the stiffening member comprising a sensor for measuring the shape of the arm.

This arrangement uses the arm axis to measure the arm shape, which simplifies the measurement. This is particularly advantageous for small diameter arms, where there is little peripheral space for placing sensors.

Furthermore, it has the advantage that the arm may be constructed by sliding links onto the stiffening member sequentially. Thus the links may engage with each other in a mechanically precise manner. The links may for example engage with each other along a hinge line, which ensure that the arm is torsionally stiff. Also, the control cables may be fed through individual or groups of links one at a time, rather than needing to be fed through the complete arm after it has been constructed, as is the case for an arm engaging with a helical spring.

The stiffening member is preferably flexible and resilient. It may be hollow or have an internal bore. This may be used to house the sensor for measuring the shape of the member, and thus the arm. The sensor may be an elongate sensor member such as an optical fibre, a plurality of optical fibres, or a single fibre with multiple cores extruded within it. The fibre may have Bragg gratings etched within each core for different strain sensing. By measuring the shape of the sensor, the shape of the arm may be calculated. It is advantageous to constrain the sensor at at least one location on each segment. This allows for the location of the ends of each segment to be sensed.

The sensor may fit tightly within the flexible member, and the stiffening member may fit tightly within the apertures in the links. Thus friction between the elements alleviates sliding movement of the elements relative to each other. In some examples, for instance where the links are long or where the links articulate through a large angle, the stiffening member may be secured to the links at predetermined locations in the arm.

Preferably, the locations at which the stiffening member is fixed are chosen to achieve a small change in the length of the member to alleviate buckling or stretch of the member and damage to the sensor within the stiffening member, and in order to optimise the shape measuring accuracy by ensuring that the number of points of inflexion in the sensor fibre between the fixed points in minimised. It has been found that fixing the stiffening member at the joints between the links helps to maintain the fixed length of the member, but concentrates the bend at one point. At the other extreme, fixing the member at the midpoints between adjacent links gives the greatest variation in length which must be accommodated by the stiffening member bending. Hence, the stiffening member is preferably fixed to the links at points between the midpoint and the joint.

Where each segment comprising a plurality of links, the stiffening member is preferably attached to each link, while the sensor may be fixed to the stiffening member at greater intervals.

There may be plurality of stiffening members provided in the channel around the longitudinal axis. Thus it is possible to achieve a specific bending stiffness which may be symmetric or asymmetric.

The hinges between adjacent pairs of links may for example be located at approximately 60° offsets. This provides a compact layout, particularly in the case where each segment has three control cables.

Thus according to a further aspect of the invention, there is provided a robotic arm comprising a plurality of sequentially arranged articulated segments, in which the articulations between the segments allow bending substantially about a hinge line across the links, in which the hinge lines are offset from each other by about 60 degrees.

Therefore the hinges are in one of three offset positions. The hinges may be arranged such that adjacent hinges are at offset angles, and progress between the three possible positions in turn. However, it is also possible that adjacent hinges may be in the same location.

BRIEF DESCRIPTION OF THE DRAWINGS

In order that the invention may be more readily understood, reference will now be made to the accompanying drawings, in which:

FIGS. 4, 5 and 6 are similar views of an arm according to another embodiment of the invention.

DETAILED DESCRIPTION OF THE INVENTION

Figure 1:
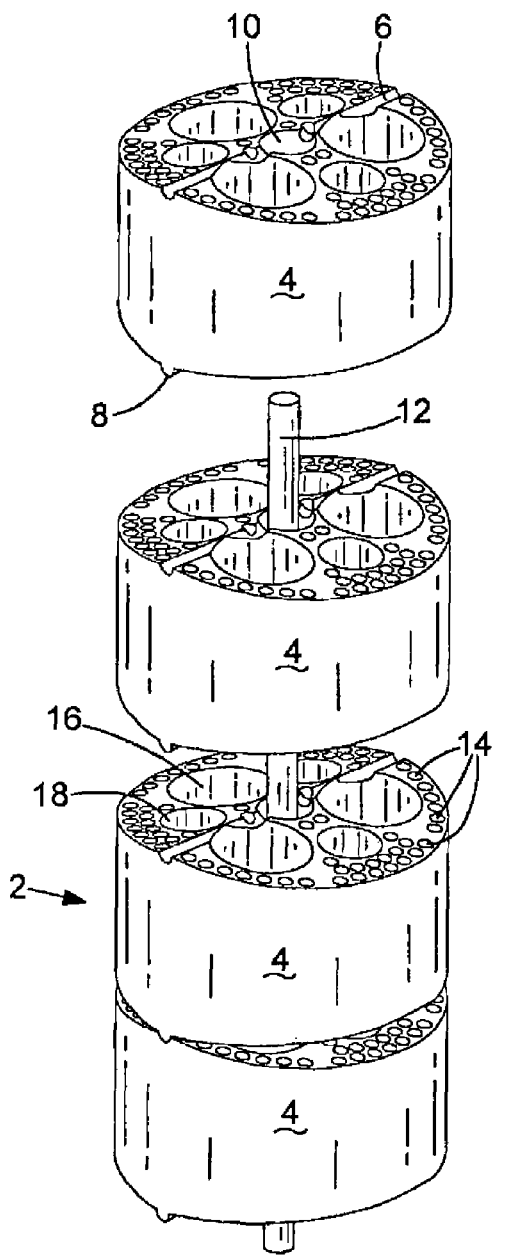
FIGS. 1, 2 and 3 are perspective, end cross-sectional, and side cross-sectional views of a part of an arm according to one embodiment of the invention.

Referring to FIG. 1, a robotic arm 2 comprising a plurality of sequentially arranged articulated links 4. The articulation are formed by hinges comprising a recess 6 extending along the diameter of one face of each link, and a corresponding projection 8 extending along the diameter of the opposite face of the adjacent link 4. The links 4 also each have a central aperture 10, extending along the axes thereof.

The arm 2 is constructed by threading the links 4 onto a stiffening member 12 through the central apertures 10. The stiffening member 12 is elongate and is formed of a resilient flexible material such as spring, steel or nitinol. The member 12 includes a sensor for measuring the shape of the member, such as an optical fibre (not shown).

The central apertures 10 may be shaped such that the member 12 is a close fit towards the middle of the link, but the opening 11 of the aperture is wider than the diameter of the member 12.

The links 4 each comprise a plurality of cable apertures 14 arranged around their circumference, for carrying control cables for controlling the position of each segment, and thus the shape of the arm. The links also include a plurality of further lumen 16, 18 which may be used for carrying services associated with work tools at the distal end of the arm.

It can be seen that, when the links fit together by the projections 8 locating in the recesses 6, the cable apertures 14 and the service lumen 16, 18 are axially aligned. It is possible to thread services cables or control cables through the links 4 individually as the arm is constructed.

Figure 2:
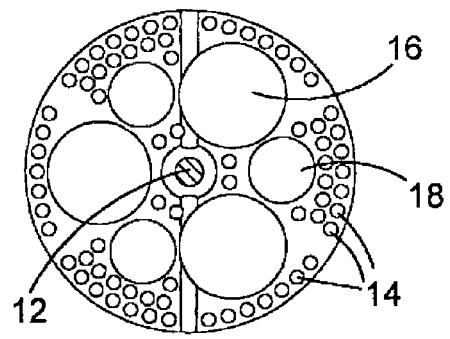
Figure 3:
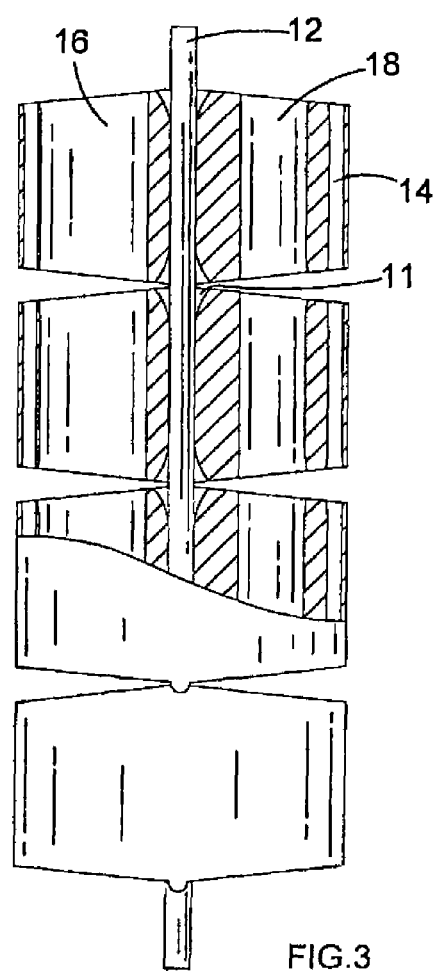

In the embodiments shown in FIGS. 1, 2 and 3, it can be seen that the projection 8 and recess 6 pairs, which act as hinges between the links 4, are aligned, such that the arm may bend in one direction about the hinges. Referring to FIGS. 4, 5 and 6, a similar construction is shown. However, in this case, the recesses 20 and projections 22 which extend along the diameter of opposite faces of the links 24 are offset with respect to each other by 60°. Each group of links forming a segment of this arrangement may have three control cables which may thus each control bending about each hinge line to give a full range of movement. In this arranged, three or six service lumen 26 may be present.

Figures 7, 8, 9:
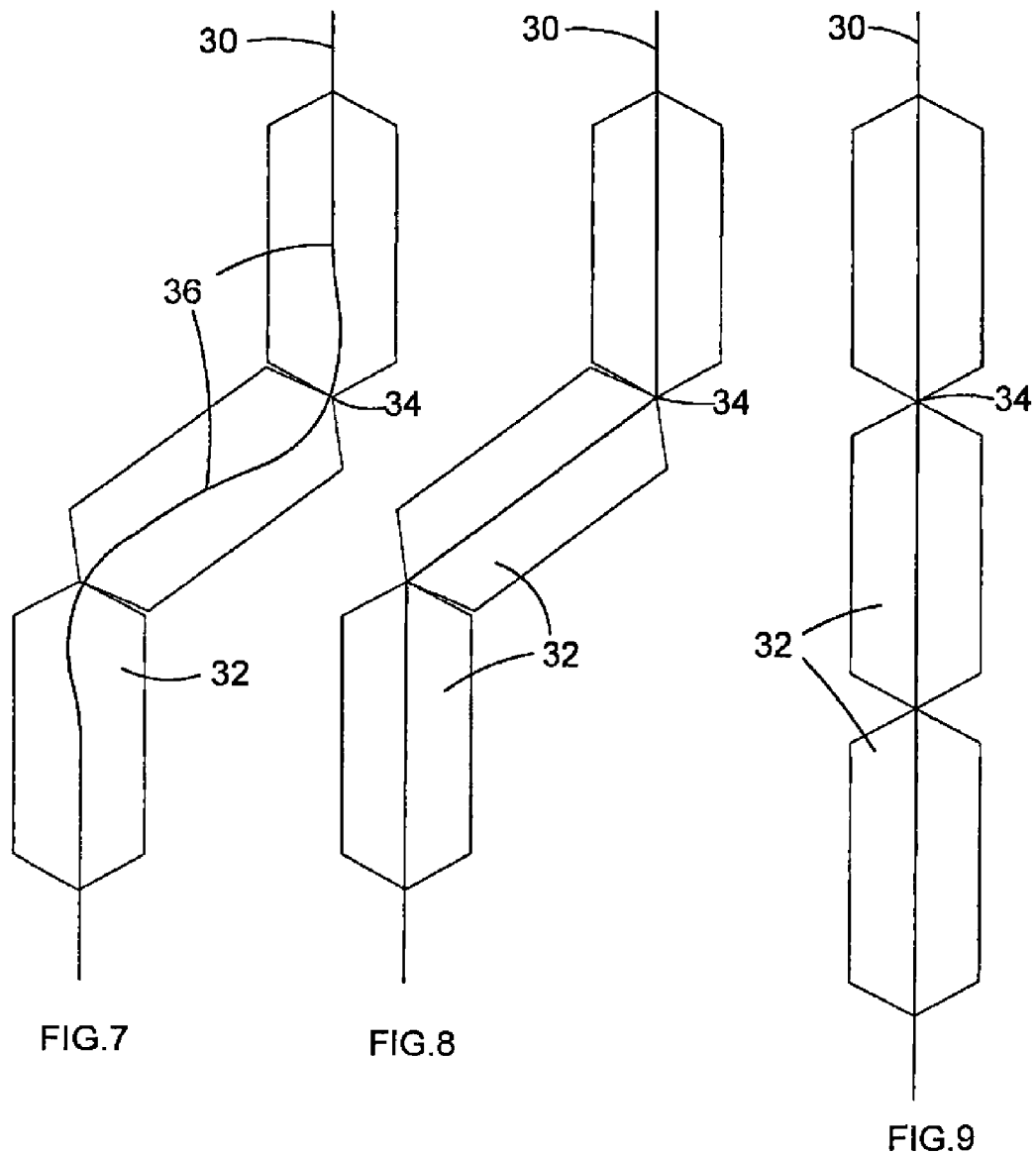
FIGS. 7, 8 and 9 are schematic side views of an arm according to the present invention, and FIG. 10 in a schematic side cross-sectional view of an arm according to an embodiment of the invention.

Referring to FIGS. 7, 8 and 9, the stiffening member 30 may be constrained or fixed in relation to each segment or link 32. FIG. 9 shows the arm in a straight configuration. If the member 30 is fixed at the articulations or joints 34, as shown in FIG. 8, then the bend is concentrated at the joint, which means the sensor must bend about a high radius of curvature, which is undesirable. If the member 30 is fixed at midpoints 36 between joints, as shown in FIG. 7, then the member 30 may bend over the distance between the points. Thus the sensor within the member 30 will not follow the arm shape so accurately, moving off the axis at the joints 34, which is also undesirable. Therefore an optimal fixing point is between these two extremes.

Figure 10:
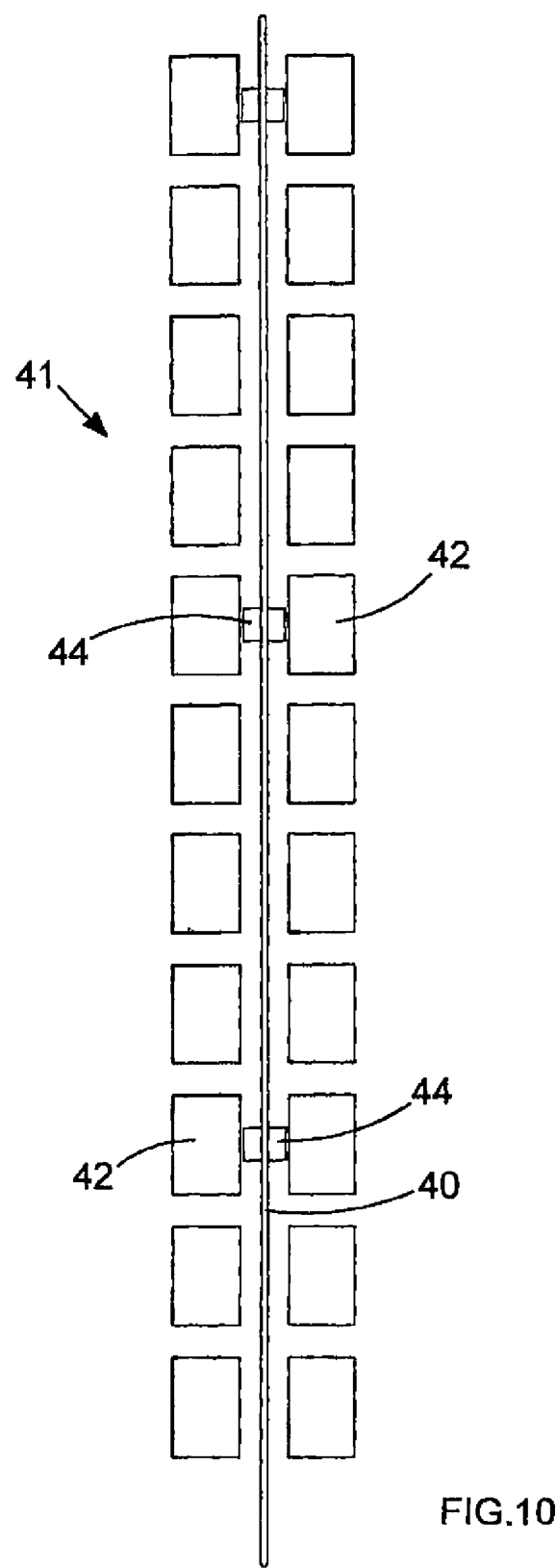

FIG. 10 shows how the stiffening member 40 including the sensor may be fixed to a section of the arm 41. Spacers 44 may be provided around the member 40 for attachment to selected links 42 at intervals along the arm.

What is claimed is:

1. A robotic arm comprising:
a plurality of sequentially arranged articulated segments, in which articulations between the segments are formed by structural hinges that extend across a substantial majority of the diameter of the segments to couple adjacent segments and allow bending substantially about a hinge line, in which the hinge lines are offset from each other by about 60 degrees;
a channel extending along the longitudinal axis of the arm, through each of the plurality of articulated segments, and an elongate stiffening member carried by the channel, the stiffening member comprising a sensor for measuring the shape of the arm, wherein the channel is flared at the ends of the articulated segments so that its flared diameter is greater than the diameter of the stiffening member;
wherein the robotic arm comprises at least three control cables that can be used to control the orientation of the articulated segments, wherein the three control cables control bending about respective hinge lines with different angular offsets.

2. A robotic arm according to claim 1, in which the stiffening member is flexible and resilient.

3. A robotic arm according to claim 1, in which the sensor is an elongate sensor member comprising at least one optical fibre.

4. A robotic arm according to claim 1, in which the sensor is constrained at at least one location on each segment.

5. A robotic arm according to claim 1, in which the stiffening member is secured to a plurality of the segments along the length of the arm.

6. A robotic arm according to claim 5 in which the stiffening member is secured to a segment at a location between the midpoint of the segment and a joint between the segment and an adjacent segment.

7. A robotic arm according to claim 1, in which each segment comprises a plurality of articulated links and the stiffening member is attached to each link, the sensor being fixed to the stiffening member at equal or greater intervals.

8. A robotic arm according to claim 1, comprising a plurality of stiffening members provided in the channel around the longitudinal axis.

* * * * *